(12) United States Patent
Patra

(10) Patent No.: US 11,742,605 B2
(45) Date of Patent: Aug. 29, 2023

(54) APPARATUS AND METHOD FOR HIGH DENSITY DETACHABLE ELECTRICAL INTERFACE

(71) Applicant: Lawrence Livermore National Security, LLC, Livermore, CA (US)

(72) Inventor: Susant Patra, Brentwood, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 257 days.

(21) Appl. No.: 17/085,440

(22) Filed: Oct. 30, 2020

(65) Prior Publication Data

US 2021/0151920 A1 May 20, 2021

Related U.S. Application Data

(60) Provisional application No. 62/941,331, filed on Nov. 27, 2019, provisional application No. 62/937,956, filed on Nov. 20, 2019.

(51) Int. Cl.
*H01L 21/00* (2006.01)
*H01R 12/77* (2011.01)
*H01R 13/02* (2006.01)

(52) U.S. Cl.
CPC ......... *H01R 12/777* (2013.01); *H01R 12/771* (2013.01); *H01R 13/025* (2013.01)

(58) Field of Classification Search
CPC ....... H01L 21/31; H01L 21/311; H01L 21/56; G03F 7/40
See application file for complete search history.

(56) References Cited

U.S. PATENT DOCUMENTS

| 4,988,305 | A | | 1/1991 | Svenkeson et al. |
| 5,810,710 | A | * | 9/1998 | Burgos ............ A61F 5/41 600/38 |
| 5,828,379 | A | * | 10/1998 | Cok ............ G06T 11/001 345/581 |
| 2002/0090862 | A1 | | 7/2002 | Berstein et al. |
| 2006/0240688 | A1 | | 10/2006 | Perugini et al. |
| 2007/0265673 | A1 | | 11/2007 | Ransbury et al. |

(Continued)

FOREIGN PATENT DOCUMENTS

WO WO-2007117538 A2 10/2007
WO WO-2010000026 A1 1/2010

OTHER PUBLICATIONS

International Search Report and Written Opinion regarding corresponding International Application No. PCT/US2020/059777, dated Mar. 3, 2021.

*Primary Examiner* — Phuong Chi Thi Nguyen
(74) *Attorney, Agent, or Firm* — HARNESS, DICKEY & PIERCE, P.L.C.

(57) ABSTRACT

The present disclosure relates to a high density electrical interconnect apparatus for interfacing with remotely located electrical components. The apparatus may have a housing, a substrate element supported within the housing, and a plurality of independent substrate interface connect subsystems arranged in a planar grid on the substrate element. The apparatus further has a plurality of independent electrical interface connector subassemblies, each configured to be coupled to an associated subplurality of the substrate interface connect subsystems, to form a plurality of electrical communication channels with the remotely located electrical components.

23 Claims, 8 Drawing Sheets

(56) References Cited

U.S. PATENT DOCUMENTS

| | | | |
|---|---|---|---|
| 2009/0164541 A1* | 6/2009 | Palma | G06T 11/005 708/290 |
| 2011/0009007 A1 | 1/2011 | Gattuso | |
| 2013/0094799 A1* | 4/2013 | Mathai | G02B 6/423 385/33 |
| 2013/0295412 A1* | 11/2013 | Izquierdo | C23C 30/00 420/90 |
| 2014/0341516 A1* | 11/2014 | Mathai | G02B 6/4259 216/26 |
| 2016/0380381 A1* | 12/2016 | Shah | H01R 13/2421 439/59 |
| 2017/0279238 A1 | 9/2017 | Spadgenske | |
| 2019/0251831 A1 | 8/2019 | Wheeler et al. | |

* cited by examiner

APPARATUS AND METHOD FOR HIGH DENSITY DETACHABLE ELECTRICAL INTERFACE

CROSS-REFERENCE TO RELATED APPLICATIONS

This application claims the benefit of U.S. Provisional Application No. 62/941,331, filed on Nov. 27, 2019, and U.S. Provisional Application No. 62/937,956, filed on Nov. 20, 2019. The entire disclosures of each of the above applications is incorporated herein by reference.

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to electrical interface systems and methods, and more particularly to embodiments for a high density electrical interface apparatus which is expandable both area-wise and height wise, and which overcomes the limitations associated with present day pin-like electrical interface systems, and which is ideally suited for biomedical applications involving electrically interfacing to large numbers of microelectrodes implanted in human tissue.

BACKGROUND

The statements in this section merely provide background information related to the present disclosure and may not constitute prior art.

There presently exists a high demand for implantable microelectrode arrays (MEAs) with high channel count. MEAs are increasingly being used in various brain-computer interface (BCI) applications. A BCI device provides collaboration between the MEAs and an external device by interpreting electrical signals received from the brain. A BCI system records the electrical signals generated within the brain from the surface of the cortex, through signaling devices implanted within the brain or from sensors placed over the scalp.

At the present time a state-of-the-art BCI system may consist of components that facilitate signal acquisition, signal enhancement, feature extraction, feature classification, and a control interface. Having a detachable interface in implantable devices is highly desirable. It allows a module-to-module electrical interface to be constructed and helps in modular design of implantable sub-systems. This modular approach also allows replacement of a defective component instead of having to discard and replace an entire, expensive system, if only one distinct portion of the system fails.

The current technology with BCI systems has two major drawbacks: (i) limit of stack size and (ii) difficulty in controlling the assembly process. Current technology such as the SYNGUS® implantable contact system, available from Bal Seal Engineering, Inc. of Foothill Ranch, Calif., are common in implantable applications such as pacemakers. These types of contact devices are typically assembled in a vertical stack that limits the number of individual contact devices that can be vertically stacked. This is because inserting a single contact pin through the assembled stack of contact devices becomes challenging due to an unfavorable aspect ratio of the path through which a contact pin must be inserted (i.e., small diameter and elongated), which can easily result in breakage of the contact pin during the assembly process. Also, inserting a contact pin through the stack is very difficult when this step is carried out during surgery because the presence of blood and tissue adds to the difficulty of handling and inserting the pin without breaking it. With an internal diameter of 0.9 mm for the contact device opening, and a length of 15 mm for the pin, the aspect ratio is 16.7. Reducing the form factor of these types of contacts makes it even more unfavorable due to an even higher probability of bending or breakage during insertion of the pin.

Another challenge is that the insertion force required to insert the contact pin is linearly dependent on the number of contacts per stack of contact devices. Thus, three linearly stacked contact devices will require about three times the insertion force needed to fully insert the contact pin when compared to inserting it through just a single contact device.

Yet another shortcoming of this linearly stacked device contact configuration is that the contact stacks (of connectors and insulators) need to be held in position by external molding. The molding process often leads to seepage of molding compound into the electrical contact area, which is very difficult to correct. Consequently, expensive assemblies are often discarded during the manufacturing process.

SUMMARY

This section provides a general summary of the disclosure, and is not a comprehensive disclosure of its full scope or all of its features.

In one aspect the present disclosure relates to a high density electrical interconnect apparatus for interfacing with remotely located electrical components. The apparatus may comprise a housing, a substrate element supported within the housing, and a plurality of independent substrate interface connect subassemblies arranged in a planar grid on the substrate element. The apparatus may further comprise a plurality of independent electrical interface connector subassemblies. Each independent electrical interface connector subassembly may include at least one of a plurality of independent pin subassemblies or a plurality of independent plug assemblies, and is configured to be coupled to an associated subplurality of the substrate interface connect subassemblies, where the subplurality of the substrate interface connect subassemblies include the other one of the plurality of independent pin subassemblies or independent plug assemblies. This enables a plurality of electrical communication channels to be formed with the remotely located electrical components.

In another aspect the present disclosure relates to a high density electrical interconnect apparatus for interfacing with remotely located electrical components. The apparatus may comprise a housing, a substrate element supported in the housing, and a plurality of independent substrate interface connect subassemblies arranged in a planar X-Y grid on a portion of the substrate element. The apparatus may further include a plurality of independent electrical interface connector subassemblies, which form at least one of a plurality of independent plug subassemblies or a plurality of independent pin subassemblies, and where the plurality of independent substrate interface connect subassemblies form the other one of the independent pin subassemblies or the independent plug subassemblies. Each pin subassembly may include a pin and an annular element electrically isolated from one another. The pin subassemblies are configured to be coupled to an associated subplurality of the plug subassemblies, to thus form a plurality of electrical communication channels therewith. A ribbon cable portion may be included to connect with each of the interface electrical connector subassemblies and interface to remote electrical components. Each plug subassembly may include first and second annular interface elements, an insulator panel and an electrically conductive coupling ring arranged to form a hole extending perpendicular to a surface of the substrate element. Each hole is configured to receive a pin of an associated one of the pin subassemblies, and to make independent electrical contact with the annular element of the associated one of the plug subassemblies, to enable a plurality of independent electrical communication channels to be formed between each pin subassembly and each plug subassembly.

In still another aspect the present disclosure relates to a method for forming a high density electrical interconnect apparatus for interfacing with remotely located electrical components. The method may comprise providing a housing, supporting a substrate element within the housing, and supporting a plurality of independent substrate interface connect subassemblies arranged in a planar grid on the substrate element. The method may further include using a plurality of independent electrical interface connector subassemblies to form a plurality of independent electrical communication channels with the substrate interface connect subassemblies, wherein each independent electrical interface connector subassembly includes at least one of a plurality of independent pin subassemblies or a plurality of plug subassemblies, and the independent substrate interface connect subassemblies comprise the other one of the plurality of independent pin subassemblies or independent plug subassemblies. The plug subassemblies and the pin subassemblies connect to form the plurality of independent electrical communication channels.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
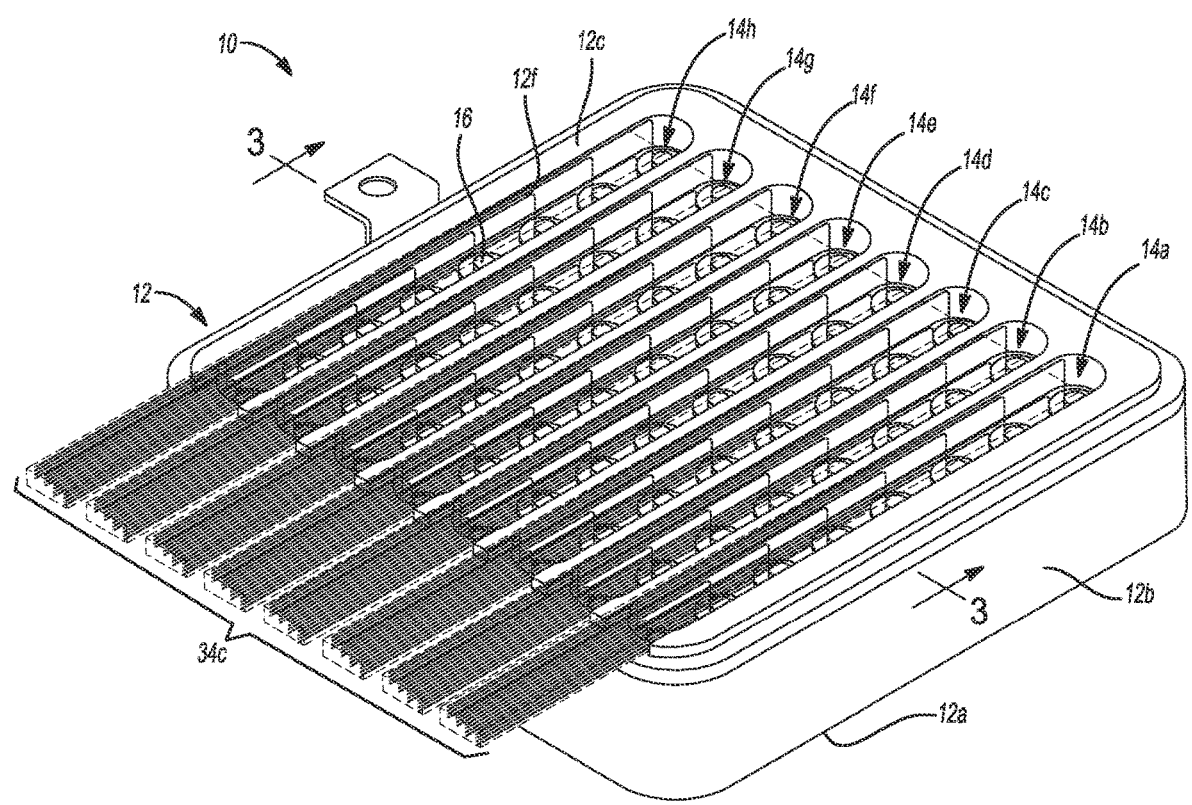
FIG. 1 is a perspective view of one embodiment of a high density interface apparatus in accordance with the present disclosure, which provides a large plurality of substrate interface connect subassemblies arranged in a planar X-Y grid, and a plurality of interface connect subassemblies for communication therewith, to provide significantly increased high connection density when electrically interfacing to large pluralities of implanted microelectrodes.
Figure 2:
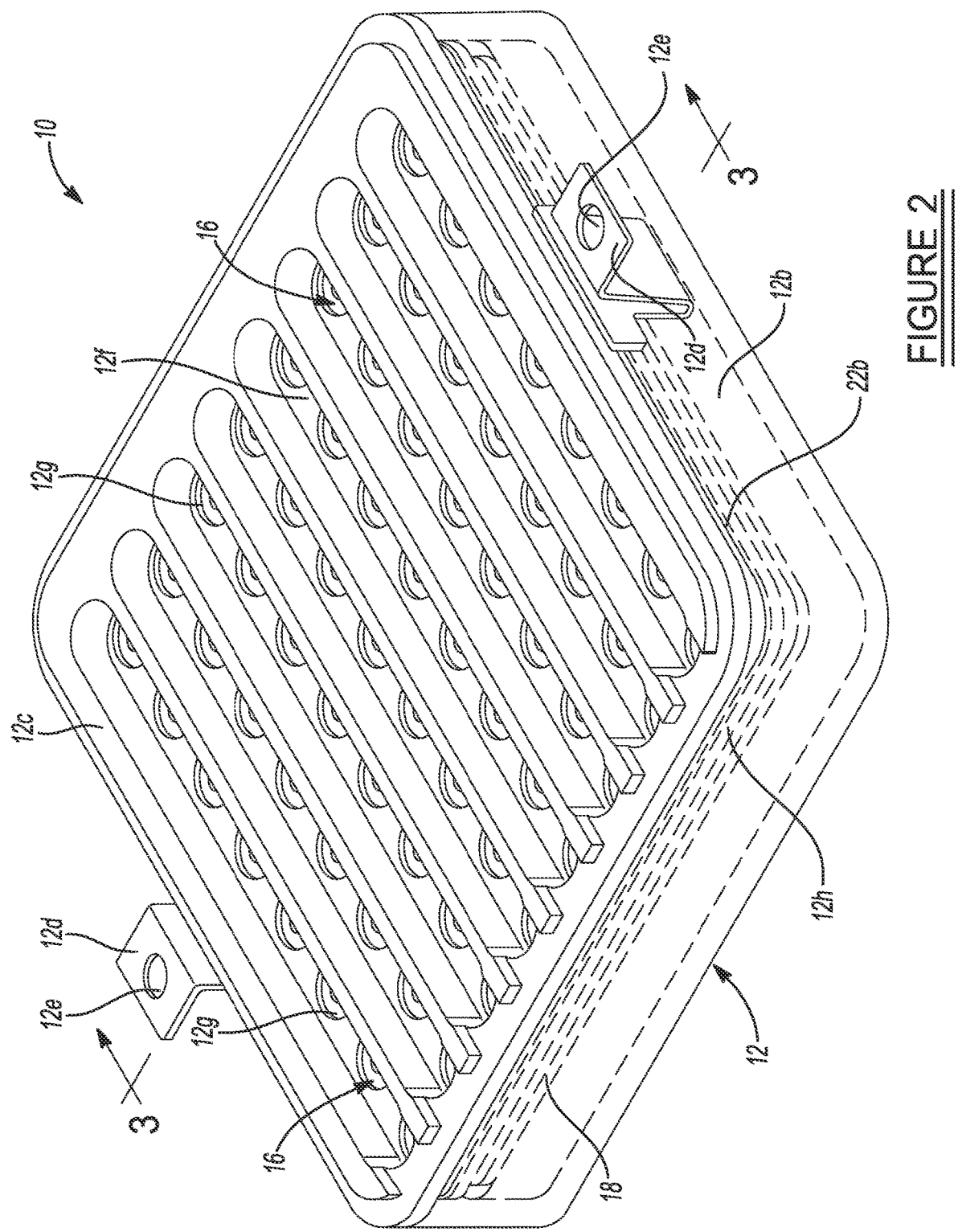
FIG. 2 is a perspective view of the apparatus of FIG. 1 but with the interface connect subassemblies removed to better illustrate the elongated recesses formed in the top wall of the housing and the openings which allow electrical communication with substrate interface subassemblies, and also with the sidewall of the housing shown translucently to help illustrate the components mounted inside the housing.

Referring to FIGS. 1 and 2 there is shown a high density interface apparatus 10 in accordance with one embodiment of the present disclosure. The apparatus 10 in this example includes a housing 12 formed from a bottom wall 12a, a sidewall 12b and a top wall portion 12c. In this example the sidewall portion has two perpendicularly extending flanges 12d with openings 12e (shown only in FIG. 2) that permit attachment of an external cover member (not shown) via conventional fasteners (e.g., threaded fasteners). A plurality of identical interface connector subassemblies 14a-14h, eight in this example, and arranged in separate elongated recesses 12f on the top wall portion 12c. The components of the housing 12 are preferably formed from a suitable high strength plastic, but other materials, for example stainless steel, may also be used. The cover (not shown), may also be plastic. Preferably the cover is attached in a manner so that the housing 12 forms a fully hermetically sealed housing.

FIG. 2 shows the housing 12 but with the interface connector ("IC") subassemblies 14a-14h omitted to better illustrate the recesses 12f. While the recesses 12f are shown as elongated linear shaped, parallel arranged recesses, this is but one example, and they could just as easily be formed in other shapes (e.g., concentric circles). Accordingly, the arrangement shown in FIG. 2 is but one example, and the apparatus 10 may be configured with a greater or lesser number of the IC subassemblies 14a-14h arranged in different patterns or groups. Each recess 12f in the top wall portion 12c includes a row of evenly spaced apart openings 12g arranged in a straight line, the purpose of which will be described in the following paragraphs. In this example eight openings 12g are formed in each recess 12f.

A principal advantage of the apparatus 10, as will become more apparent in the following description, is that the apparatus can be expanded, both area-wise and height-wise, to incorporate a significantly greater number of interface connector subassemblies to meet the needs of different applications. This provides the apparatus 10 with a high degree of modularity to meet the needs of different applications.

Figure 3:
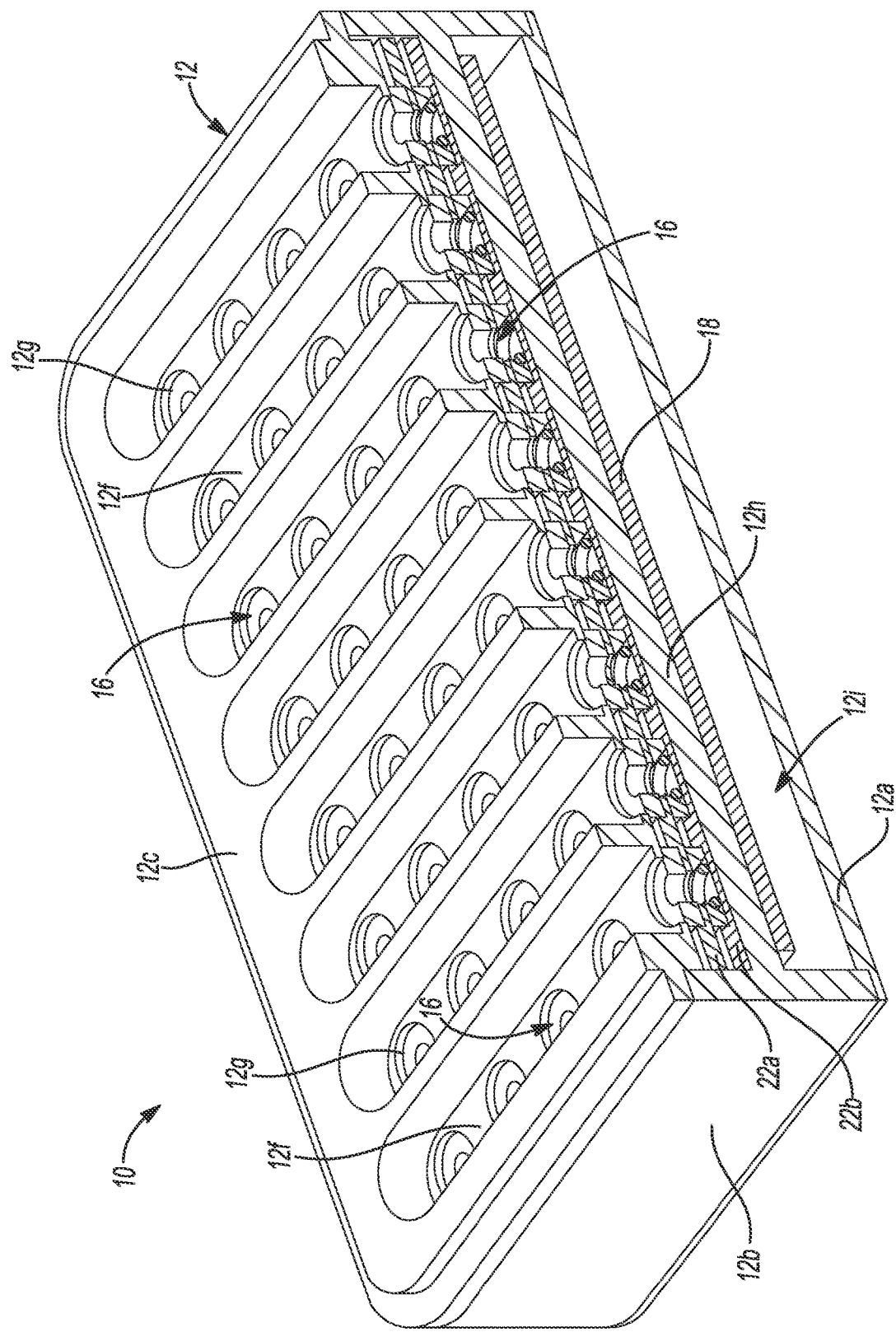
FIG. 3 is a cross sectional perspective view of the interface stack of FIG. 4 taken in accordance with directional line 3-3 in FIG. 1.

FIG. 3 shows a cross-sectional view of a portion of the apparatus 10 of FIG. 2 to illustrate a plurality of substrate interface connect subassemblies 16 ("SI connect" subassemblies). The SI connect subassemblies 16 are partially visible in FIG. 2 as well, and in this embodiment form a plurality of plug subassemblies arranged in parallel rows, with the example of FIGS. 2 and 3 showing eight separate rows. Accordingly, underneath each recess 12f in the top wall portion 12c is located eight separate ones of the SI connect subassemblies 16 arranged in a straight line, with each SI subassembly being located below an associated one of the openings 12g. The SI connect subassemblies 16 are collectively supported on, and in electrical communication with, a planar substrate element 18. The planar substrate element 18 may be supported from an interior wall portion 12h having suitable openings therein (not visible) to enable electrical connections to be made between the substrate interface subassemblies 16 and one or more electronic components (memory, controller, input/out communication circuit, etc.) which may be located in area 12i of the housing 12.

Figure 4:
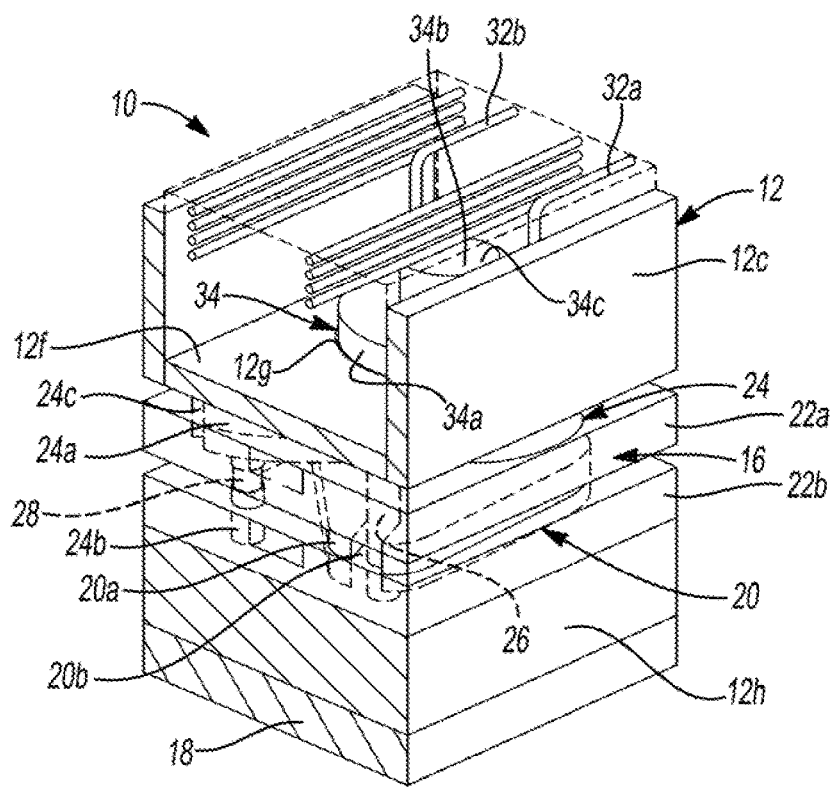
FIG. 4 is a high level perspective illustration showing the components of one of the substrate interface connect subassemblies, as well as the attachment of one of the interface connect pin subassemblies thereto.
Figure 5:
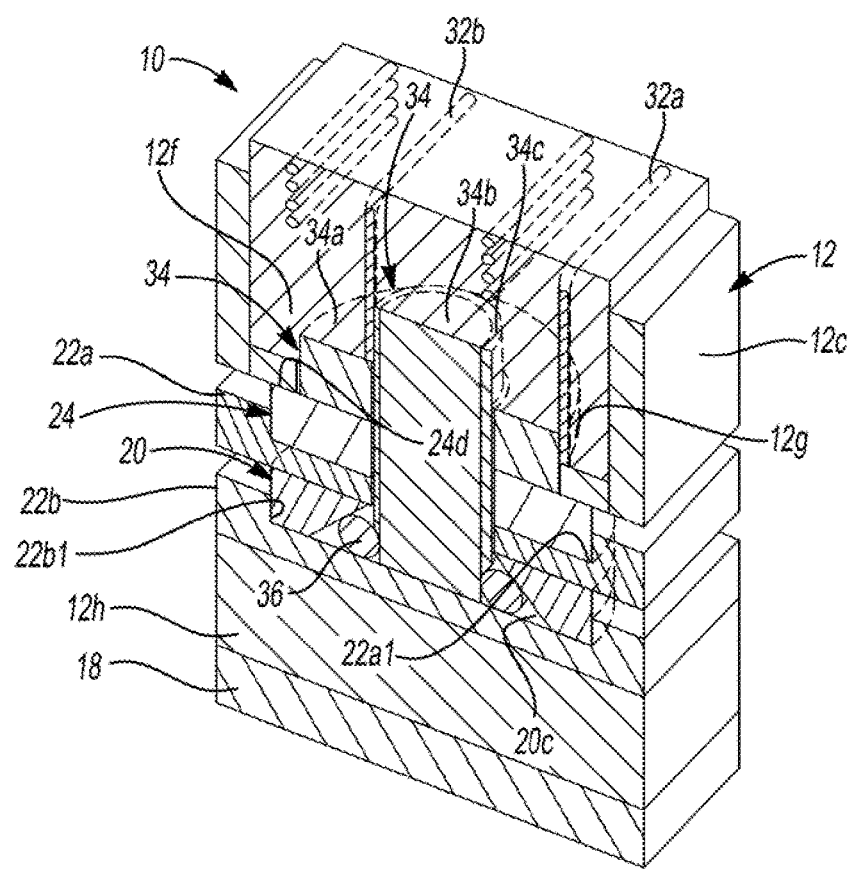
FIG. 5 is a cross-sectional side view taken in accordance with section arrow 5-5 in FIG. 4 showing the internally housed electrical coupling ring of the substrate interface connect subassembly.

FIGS. 4, 5, 6a and 6b illustrate the construction of the SI connect subassemblies 16 in greater detail. Each SI connect subassembly 16 includes an annular first interface element 20, upper and lower electrical insulator panels 22a and 22b positioned in axial alignment with the first interface element 20, and an annular second interface element 24, seated on the upper insulator panel 22a, and axially aligned with the first interface element 20. The axial alignment of components 20, 22a, 22b and 24 is illustrated in FIGS. 5 and 6. The annular first and second interface elements 20 and 24 are preferably metallic, and are thus are electrically conductive. A typical material for the annular interface elements 20 and 24 is copper, although virtually any electrically conductive material may be used.

As shown in FIG. 4, the first interface element 20 includes a laterally projecting portion 20a having a slot 20b, while the second interface element similarly has a projecting arm 24a and a leg 24b having a slot 24c. The slot 20b receives a first electrically conductive feed through pin 26, while the slot 24c receives a second electrically conductive feed through pin 28. Thus, the first feed through pin 26 places the first interface element 20 in electrical communication with an electrical circuit trace or element (not shown) being carried on the substrate element 18. Similarly, the second feed through pin 28 places the second interface element 24 in electric communication with a separate circuit trace or element (not shown) in the substrate element 18, and thus forms a second independent communication path through the substrate. Thus, it will be appreciated that each of the SI connect subassemblies 16 provides two independent communication paths to associated electrical traces or conductors in (or on) the substrate element 18.

Figure 7:
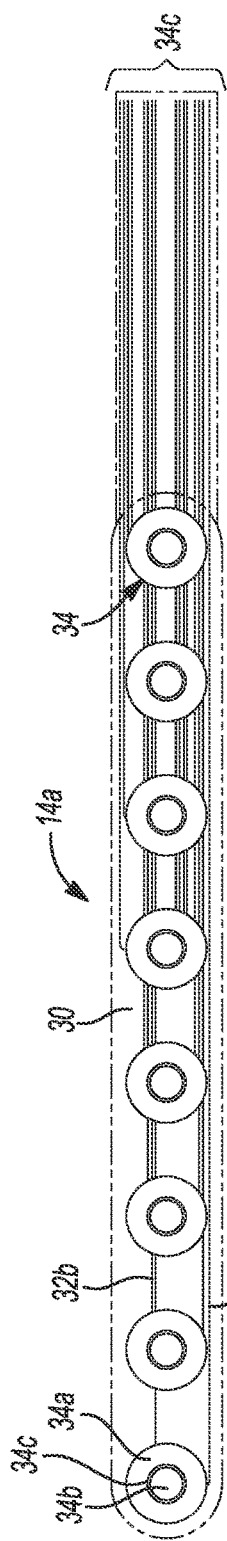
FIG. 7 is a bottom plan view of one of the interface connect subassemblies showing eight independent pin subassemblies, forming sixteen independent communication channels, with the pin assemblies arranged in a straight path.
Figure 8:
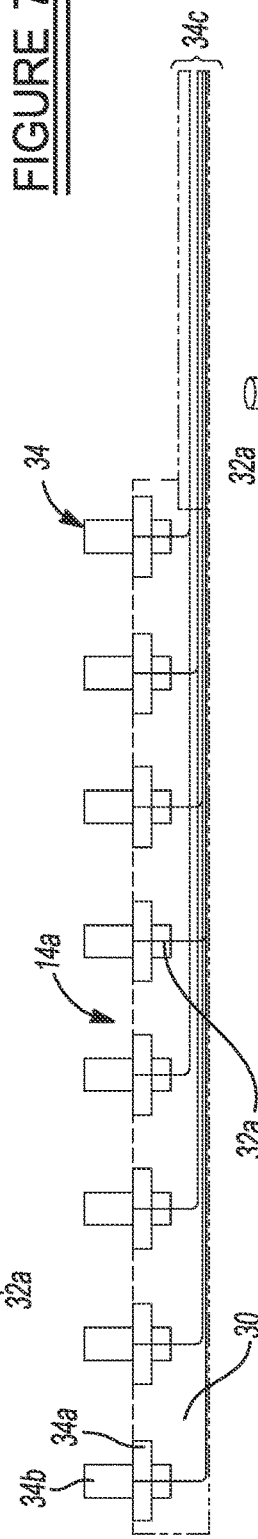
FIG. 8 shows the interface connect subassembly of FIG. 7 but from a side view in accordance with directional line 8-8 in FIG. 7.
Figure 8A:
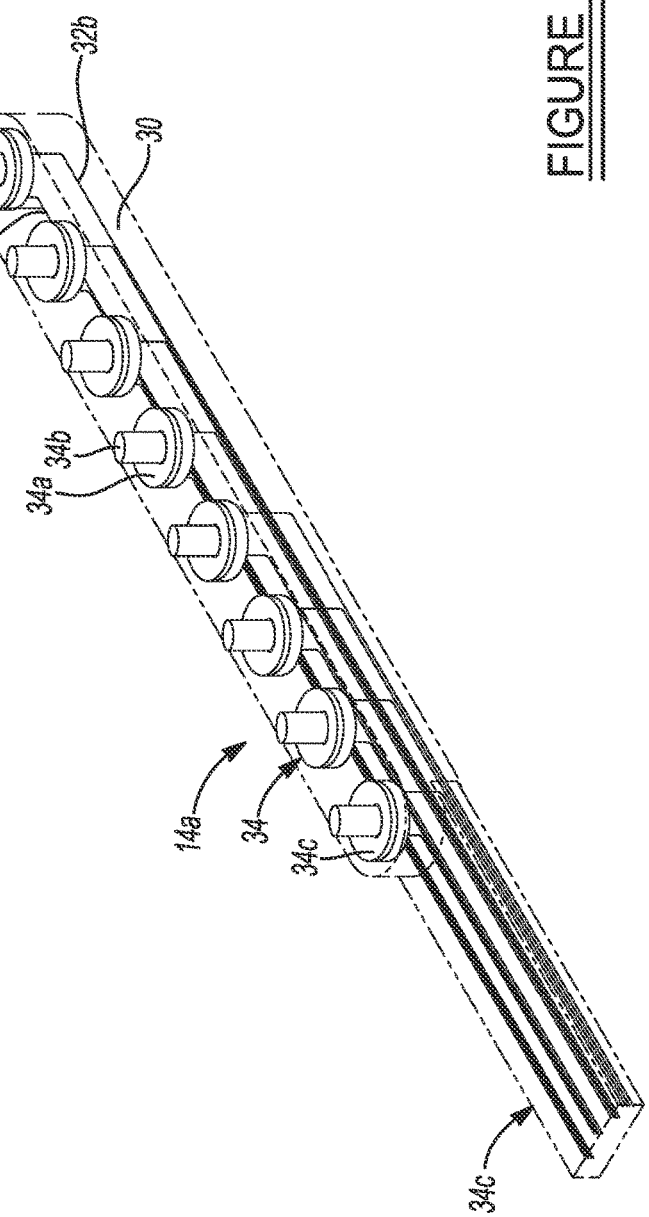
FIG. 8a shows the interface connect subassembly of FIG. 7 from a perspective view.

Referring to FIGS. 7, 8 and 8a, one of the IC subassemblies 14a is shown in greater detail. The IC subassemblies 14a-14h in this example form pin subassemblies. The IC subassemblies 14a-14h in this example are further all identical in construction, so only the construction for IC subassembly 14a will be described. The IC subassembly 14a includes an over-molded substrate 30, which may be comprised of plastic or another other suitably strong yet electrically insulative material, which supports or substantially encases a plurality of groups of electrical conductors 32a and 32b. One each of conductors 32a and 32b (i.e., one pair consisting of one conductor 32a and one conductor 32b) is coupled to a pin subassembly 34. The IC subassembly 14a in this example includes eight independent, spaced apart pin subassemblies 34. Each pin subassembly 34 includes a ring-like, annular element 34a and perpendicularly arranged pin 34b. The annular element 34a and the pin 34b are separated by a portion of the over-molded substrate 30 material (i.e., typically plastic) which forms an insulative bushing-like component 34c that physically and electrically separates the annular element 34a and the pin 34b. As such, one conductor 32a is electrically coupled to the annular element 34a, and one conductor 32b is electrically coupled to the pin 34b. This enables each pin subassembly 34 to communicate two independent electrical signals received from its associated pair of conductors 32a and 32b to an associated one of the SI connect subassemblies 16. Alternatively, each pin subassembly 34 can be used to transmit signals received via its associated SI connect subassembly 16 out to external elements (e.g., probe-like elements) that may be implanted in human tissue, and thus be used to apply excitation signals to an area of an anatomy. Still further, one of the conductors 32a or 32b may be used to receive a signal which is transmitted through the SI connect subassembly 16, while the other conductor is used to transmit a signal received from the SI connect subassembly out over the other one of the two conductors 32a or 32b. All of the conductors 32a and 32b are grouped into a ribbon cable portion 34c which may extend longitudinally from one end of the over-molded substrate 30, and in longitudinal alignment with the over-molded substrate, to other implantable probe-like elements. Thus, each IC connect subassembly 16 provides sixteen independent communication channels, or in other words two channels associated with each pin subassembly 34.

Figure 6A:
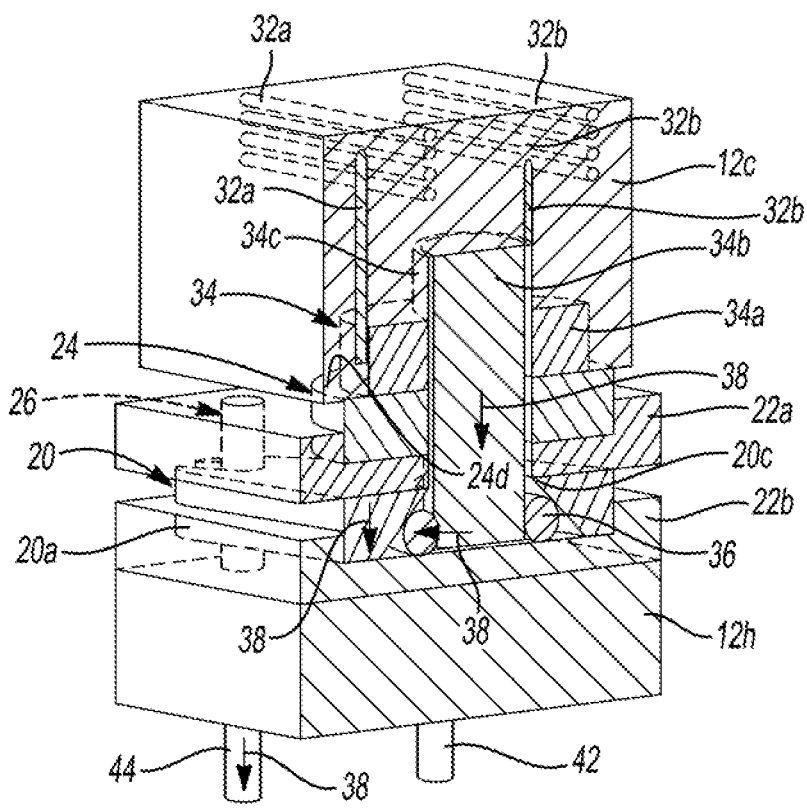
FIGS. 6a and 6b are perspective cross sectional views of the apparatus from orientations different from that shown in FIG. 5, and showing arrows illustrating the two separate electrically conductive paths formed through the substrate interface connect subassembly when one of the pin subassemblies is coupled thereto.
Figure 6B:
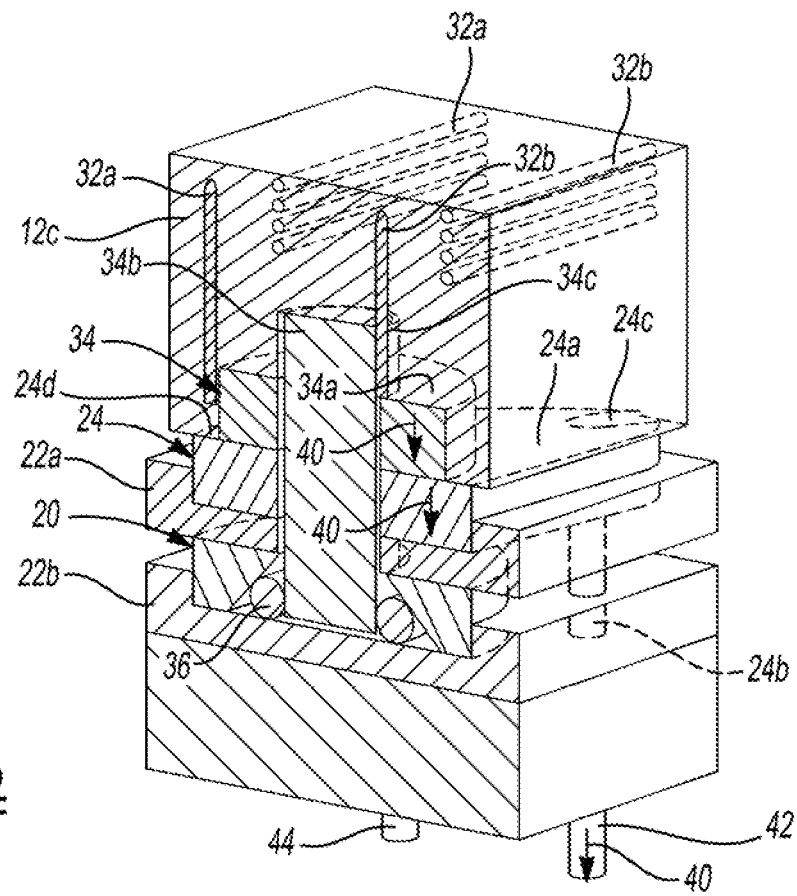

With further reference to FIGS. 4, 5, 6a and 6b, the connection between a single one of the SI connect subassemblies 16 and one of the pin subassemblies 34 can be seen. In FIGS. 5, 6a and 6b, each SI connect subassembly 16 can also be seen to include an electrically conductive coupling ring 36, which is seated within a beveled inner wall portion 20c of the first interface element 20. The coupling ring 36 has a slightly smaller internal diameter than the components 20, 22 and 24 such that it projects slightly into the linear hole formed by the axially aligned components 20, 22a and 24. The electrically conductive coupling ring 36 is a commercially available component. The annular element 34a and the pin 34b are shown in FIGS. 4, 6a and 6b without the over-molded substrate 30 to help illustrate the electrical connection that is made with the SI connect subassembly 14a. When the pin subassembly 34 is fully assembled on to the SI connect subassembly 16, the pin 34b extends through an axial opening formed by the components 20, 22a and 24, and through the electrically conductive coupling ring 36 (FIGS. 5-7), and makes electrical contact with the electrically conductive coupling ring 36. This creates a continuous electrical communication path (i.e., channel) through the pin 34b, the electrically conductive coupling ring 36, the first interface element 20, the first feed through pin 26, and a circuit trace or conductor (not shown) which is mounted on (or housed within) the substrate element 18. This connection path is illustrated in FIG. 6a by arrows 38. The annular element 34a, however, makes contact with a planar surface 24c of the second interface element 24, which is in electrical contact with the second interface element 24, the second feed through pin 28, and a separate electrical conductor or circuit trace (not shown) mounted in the substrate element 18. This connection thus forms a continuous, second communications path or channel which is denoted by arrows 40 in FIG. 6b. The two independent electrical connections described immediate above are created by simply pressing the pin 34b into the axial opening of the SI connect subsystem 16 until the annular element 34a seats on the second annular interface element 24.

With brief reference to FIGS. 3 and 5, during assembly the lower insulator panel 22b is initially installed on the interior wall portion 12h of the housing 12. Each one of the first interface elements 20 is seated within an associated recess 22b1 in the lower insulator panel 22b, with its associated electrically conductive coupling ring 36 housed within it, and contacting the planar surface 20c. The upper insulator panel 22a is then installed over all of the first interface elements 20. Each one of the second interface elements 24 is then seated in an associated recess 22a1 in the upper insulator panel 22a. Top wall portion 12c is then placed over all of the second interface elements 24 which serves to clamp them together. The IC subassemblies 14a can then all be installed so that the pin subassemblies 34 make contact with the electrically conductive coupling rings 36 and the second interface elements 24. Finally, a cover member (not shown) secured over the top wall portion 12c.

With further reference specifically to FIGS. 6a and 6b, the two communication channels from each SI connect subassembly 16 may be coupled via suitable pins 42 and 44 assembled into the substrate element 18 to an external mating electrical connector (not shown), which is in turn coupled to one or more other electronic subsystems such an input/output interface of a microcomputer. In one example, the mating electrical connector may be positioned in area 12i of the housing 12. Optionally, a portion of, or all of, the electronics communicating with the SI subsystems 16 may also be located within the area 12i of the housing 12.

Figure 9:
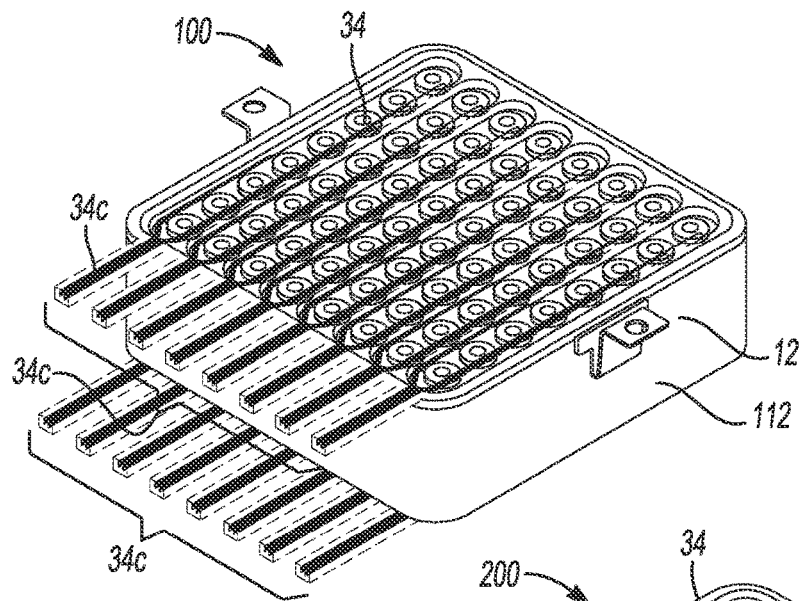
FIG. 9 shows another embodiment of a high density electrical interconnect apparatus in accordance with the present disclosure which makes use of two planar, vertically arranged layers of interconnects, essentially forming a two layer implementation of the apparatus of FIG. 1.

FIG. 9 shows an apparatus 100 in accordance with another embodiment of the present disclosure, which forms a two layer high density electrical interconnect apparatus. The apparatus 100 essentially takes two of the apparatuses 10 shown in FIG. 1 and couples the housing portions 12 and 112 together, to double the interconnect capacity without increasing the length×width footprint of the apparatus. All of the ribbon cable portions 34c of the IC subassemblies 14 extend from one side of the apparatus 10. In this regard it will also be appreciated that the housing 12 and the housing 112 may be formed with a mating ledges or other features that enable the housing 12 to be centered on the housing 112 during assembly. Separate connecting elements or features (not shown) may be used to removably couple the two housing sections 12 and 112 together.

Figure 10:
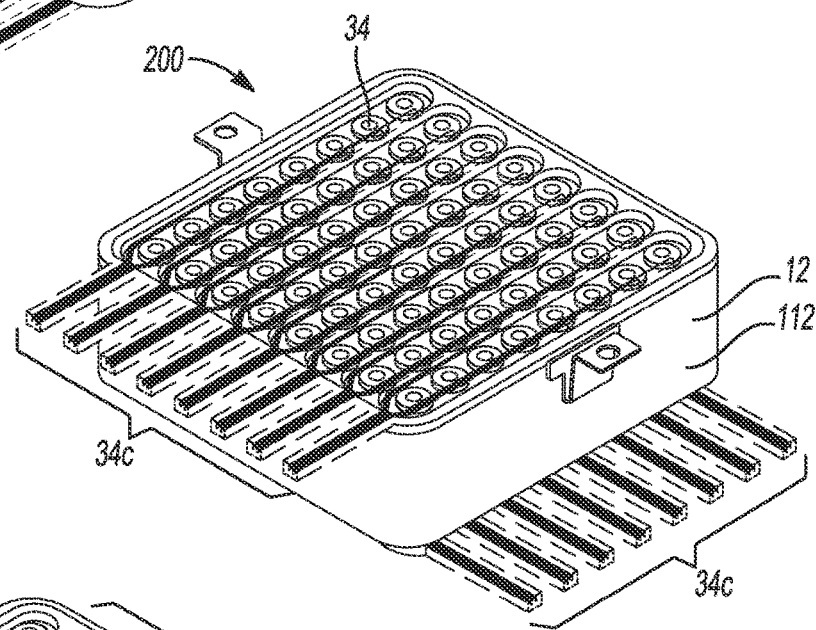
FIG. 10 shows another embodiment of the present disclosure which is similar to that shown in FIG. 9, but with the ribbon cable portions of the interconnect subsystems extending perpendicularly out from the two layers of interconnects.

FIG. 10 shows an apparatus 200 which is similar to the apparatus 100 but has the ribbon cable portions 34c from housings 12 and 112 extending from perpendicular walls of the apparatus.

Figure 11:
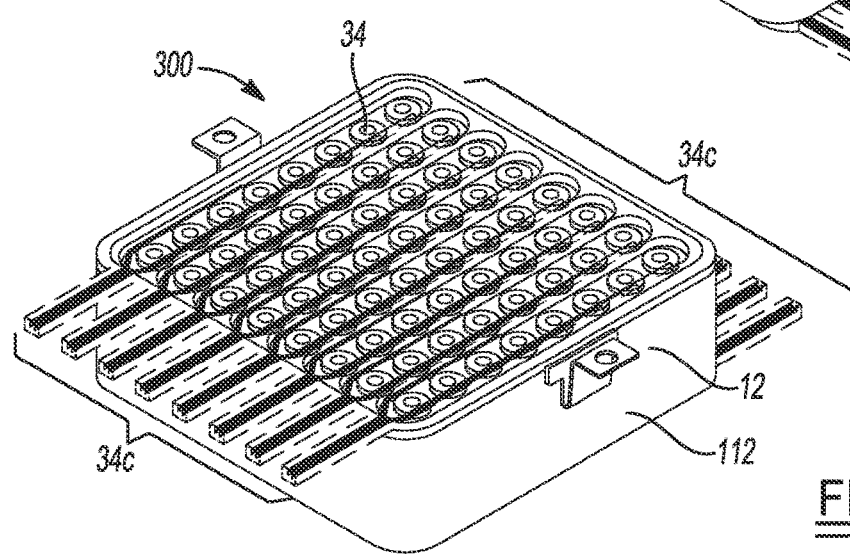
FIG. 11 is another embodiment of the apparatus of the present disclosure which is similar to FIG. 10, but with the ribbon cable portions extending out from the apparatus in opposite directions.

FIG. 11 shows an apparatus 300 which is similar to the apparatus 200 but has the ribbon cable portions 34c extending from oppositely facing wall portions of the apparatus housings 12 and 112.

From FIGS. 9-11 it will be appreciated that an even greater multi-layer apparatus may be constructed which has three, four or more distinct layers of the apparatus 10 coupled together. Such would provide dramatically increased connection density without increasing the length by width footprint of the assembled apparatus.

Figure 12:
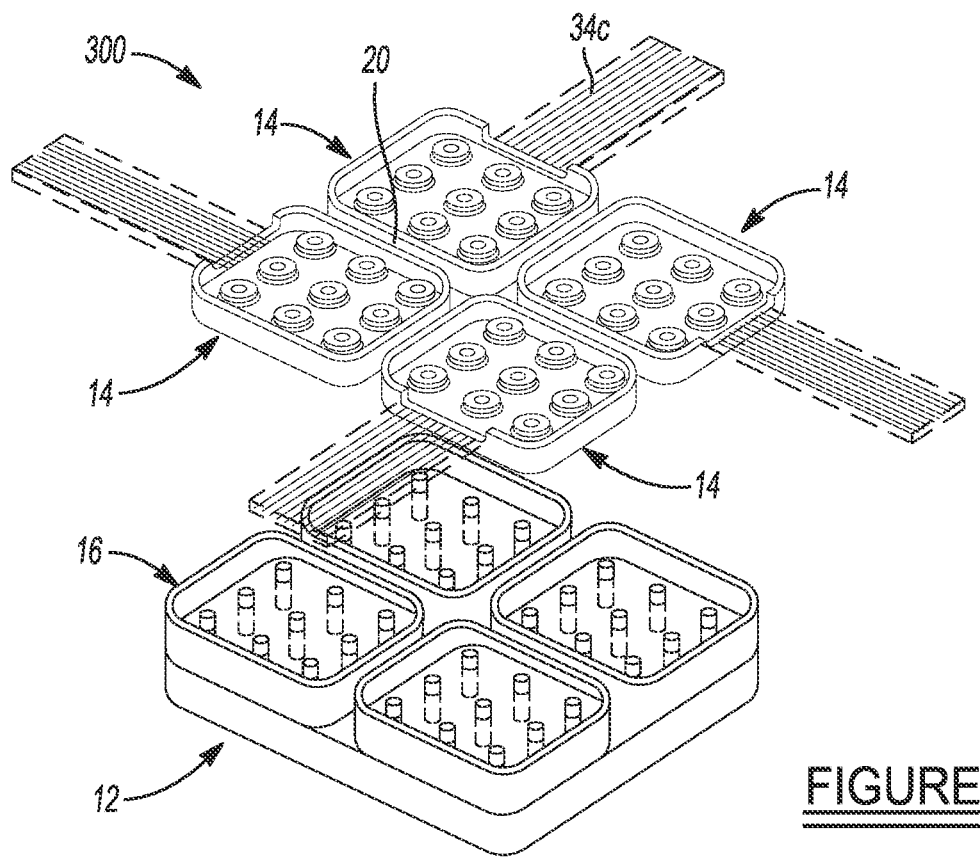
FIG. 12 is an exploded perspective view of an electrical interconnect apparatus in accordance with another embodiment of the present disclosure in which a plurality of pin subassemblies are fixedly mounted in a substrate assembly, and a plurality of independent plug assemblies are configured to be pressed onto the pin subassemblies.
Figure 13:
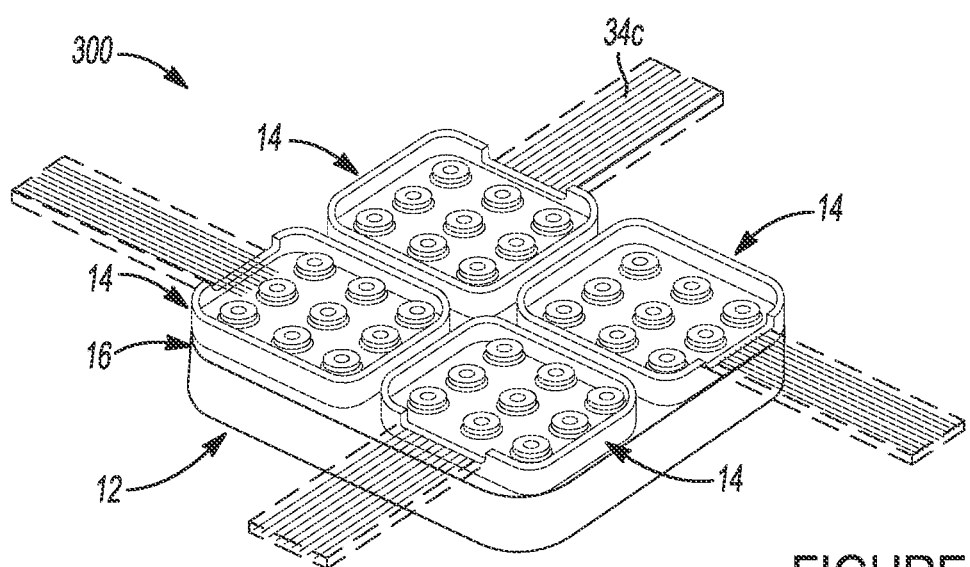
FIG. 13 is an assembled view of the apparatus of FIG. 12.

FIGS. 12 and 13 illustrate an apparatus 300 in accordance with another embodiment of the present disclosure. The construction of the apparatus 300 is similar to the apparatus 10 but the positions of the SI connect subassemblies 14 and the interface connector subassemblies 16 are reversed; instead the SI connect subassemblies 14, which form plug subassemblies in this embodiment, are the separable portions, and the interface connector subassemblies 16, which form pin subassemblies in this embodiment, are fixedly mounted in the housing 12. Otherwise the constructions of the subsystems 14 and 16 are substantially the same. One specific difference is that the SI connect subassemblies 14 are configured as a 3×3 grid of interface elements 20 each forming a plug assembly, with the ribbon cable 34c communicating electrical signals between all of the remote electrical components and the interface connector subassemblies 16. Similarly, the interface connector subassemblies 16 are configured in segmented groups of nine pin subassemblies. However, it will be appreciated that the apparatus 300 is not limited to a 3×3 array. For example for a 64 connection array, the apparatus 300 can be configured with the interface connector subassemblies 16 in a 4×4 group, or a 2×8 group instead of the illustrated 3×3 configuration. The modular design of the system 300 enables virtually any combination/layout of array to be formed to meet the needs of a specific implementation.

The present apparatus 10 and method overcomes the disadvantage present with the large aspect ratio of conventional interconnect systems presently in use in biomedical applications. An important benefit of the pin subassemblies 34 is that the aspect ratio of the pin 34b length relative to its thickness can be kept to about 2-1, or possibly even closer to 1-1. This is important considering that the diameter of the pin 34b is typically less than 1 millimeter when using a high density interconnect device in biomedical applications. With an aspect ratio of pin length to thickness of about 2-1, the pin subassemblies 34 can be attached much more easily and with much less chance of bending the pin portion 34b, as compared to conventional pin connection assemblies, which often require an aspect ratio of pin length to thickness of 6-1, 8-1 or even greater. The desirable 2-1 aspect ratio of each pin 34b of the apparatus 10 enables the attachments to be made easily even in demanding applications, such as during surgery, where a surgeon's fingers may be covered with fluids such as blood, thus making handling and insertion of traditional high aspect ratio pin connector elements challenging. The shorter aspect ratio of the pin subassembly 34 described herein also dramatically reduces the possibility that a pin will be bent during insertion or handling, and thus not make full electrical contact with the mating conductive surfaces that the pin needs to contact over its length.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A high density electrical interconnect apparatus for interfacing with remotely located electrical components, the apparatus comprising:
    a housing having a plurality of recesses each having a predetermined configuration;
    a substrate element supported within the housing;
    a plurality of independent substrate interface connect subassemblies arranged in a planar grid on the substrate element; and
    plurality of independent electrical interface connector subassemblies, each said independent electrical interface connector subassembly including:
        an over-molded substrate shaped generally in accordance with the predetermined configuration of the recesses of the housing, so as to fit within and be housed within an associated one of the recesses of the housing;
        at least one of a plurality of independent pin subassemblies or a plurality of independent plug assemblies housed by the over-molded substrate, and configured to be coupled to an associated subplurality of the substrate interface connect subassemblies, where the subplurality of the substrate interface connect subassemblies include the other one of the plurality of independent pin subassemblies or independent plug assemblies, and are held in a fixed arrangement by the over-molded substrate enabling communication with a subplurality of the plurality of independent substrate interface connect subassemblies, to form a plurality of electrical communication channels with the remotely located electrical components; and
        a cable assembly extending into the over-molded substrate, and communicating with each one of the plurality of independent pin subassemblies or each one of the plurality of independent plug assemblies.

2. The apparatus of claim 1, wherein the pin subassemblies are segmented into separate groups, and the pin subassemblies of each said separate group are arranged to form a straight line.

3. The apparatus of claim 1, wherein the substrate interface connect subassemblies are arranged in an X-Y grid on the substrate element.

4. The apparatus of claim 1, further comprising an additional housing section including an additional plurality of substrate interface connect subassemblies and an associated additional subplurality of interface connector subassemblies, the additional housing being the same in length and width as the housing and being positioned on the housing to form a multilayer, high density electrical interconnect apparatus.

5. The apparatus of claim 1, wherein the plug subassemblies are segmented in a plurality of separate groups, with each said separate group comprising a plurality of plugs arranged in a grid.

6. The apparatus of claim 5, wherein the cable assembly of each one of the independent electrical interface connector subassemblies includes a ribbon cable portion including a plurality of electrical conductors.

7. The apparatus of claim 1, wherein each one of the independent electrical interface connector subassemblies includes:
a plurality of electrical conductors associated with the cable assembly;
the over-molded housing portion further supporting each of at least one of the plurality of independent pin subassemblies or each one of the plurality of independent plug subassemblies in a linear spaced apart arrangement; and
the cable assembly including a ribbon cable portion extending from the over-molded housing for supporting a portion of the electrical conductors.

8. The system of claim 1, wherein the photo-sensitive resin comprises a photo-sensitive resin bath.

9. The system of claim 1, further comprising a projection lens for scaling the at least one of the optical initiation images and the at least one of the optical inhibition images in accordance with selected dimensions for the 3D part.

10. A system for forming a three dimensional (3D) part, the system comprising:
a first electronic controller;
a digital mask subsystem having a plurality of electronically individually addressable pixels;
a 3D model in communication with the first electronic controller;
a beam delivery subsystem responsive to the first electronic controller for generating first and second optical signals, the beam delivery subsystem including;
a first light source for generating a first optical signal;
a second light source for generating a second optical signal;
a beam splitter for receiving the first and second optical signals and directing the first and second optical signals in a first direction toward the digital mask subsystem;
the beam splitter further configured to receive the first and second optical signals from the digital mask subsystem and to direct the first and second optical signals in a second direction therethrough towards the digital mask subsystem; and
a beam delivery electronic controller in communication with the first electronic controller, and configured to control the first and second light sources;
the first electronic controller configured to control the digital mask subsystem to receive the first and second optical signals from the beam splitter, and the 3D model, and to create from the 3D model and the first optical signal a primary 2D image, the primary 2D image being transmitted through the beam splitter in a second direction opposite to the first direction, and generated for a first predetermined time period and causing activation of a polymerization species of a photo-sensitive resin in accordance with illuminated areas of the primary 2D image, to thus cause polymerization of select portions of the photo-sensitive resin, within a predetermined depth of the photo-sensitive resin, to initiate formation of a first layer of the 3D part;
the first electronic controller further configured to control the digital mask subsystem to receive at least one of the second optical signals and to create therefrom a secondary 2D image, the secondary 2D image being projected through the beam splitter in the second direction, and for a second predetermined time period, the secondary 2D image being a negative of the primary 2D image, and which is projected in the same predetermined depth of the photo-sensitive resin, as the primary 2D image, and which initiates stimulated emission depletion of select subportions of the polymerization species within the same predetermined depth as the primary 2D image, over at least portions of the first layer, where the select subportions defined by the secondary 2D image were previously illuminated using the primary 2D image, to enhance resolution of one or more select portions of the photo-sensitive resin in the same predetermined depth;
wherein the primary 2D image and the secondary 2D image differ from one another and are created in alternating fashion using the digital mask subsystem to form each layer of the 3D part; and
wherein the primary 2D image and the secondary 2D image are both projected into an upper surface of the photo-sensitive resin.

11. The system of claim 10, further comprising:
a spatial light modulator responsive to the electronic controller; and
the digital mask subsystem and the spatial light modulator cooperating to create the primary and secondary 2D images from the first and second optical signals, respectively.

12. The apparatus of claim 1, wherein the housing includes upper and lower electrical insulator panels; and
wherein each one of the substrate interface connect subassemblies includes:
an annular first interface element positioned on the lower insulator panel;
an electrically conductive coupling ring positioned on an inner wall of the annular first interface element;
the upper electrical insulator panel positioned on the annular first interface element;
an annular second interface element positioned on the upper electrical insulator panel; and
the annular first interface element, the electrically conductive coupling ring and the annular second interface element being axially aligned to provide a hole therethrough.

13. The apparatus of claim 12, wherein the inner wall of the annular first interface element comprises a beveled wall portion, and wherein the coupling ring is supported on the beveled wall portion.

14. The system of claim 1, wherein the digital mask subsystem further includes a spatial light modulator for modulating the optical signals received from the beam delivery subsystem.

15. The apparatus of claim 14, further comprising a separate first feed through pin disposed in the slot of each said annular first interface element, and extending into electrical contact with an element carried by the substrate element.

16. The system of claim 1, further comprising a 3D computer aided design (CAD) modeling system for supplying a 3D model of a part to the digital mask subsystem.

17. The apparatus of claim 16, further comprising a separate second feed through pin disposed in the slot of each said annular second interface element, and extending into electrical contact with an element carried by the substrate element.

18. A high density electrical interconnect apparatus for interfacing with remotely located electrical components, the apparatus comprising:
- a housing;
- a substrate element supported in the housing;
- a plurality of independent substrate interface connect subassemblies arranged in a planar X-Y grid on a portion of the substrate element;
- a plurality of independent electrical interface connector subassemblies, each said independent electrical interface connector subassembly including:
  - at least one of a plurality of independent plug subassemblies or a plurality of independent pin subassemblies, and where the plurality of independent substrate interface connect subassemblies form the other one of the independent pin subassemblies or the independent plug subassemblies;
- each said pin subassembly including a pin and an annular element electrically isolated from one another; and the pin subassemblies configured to be coupled to an associated subplurality of the plug subassemblies, to form a plurality of electrical communication channels therewith; and
  - a ribbon cable portion configured to be connected to remotely located electrical components;
- each said plug subassembly including first and second annular interface elements, an insulator panel and an electrically conductive coupling ring arranged to form a hole extending perpendicular to a surface of the substrate element, and
- each said hole configured to receive a pin of an associated one of the pin subassemblies, and to make independent electrical contact with the annular element of the associated one of the plug subassemblies, to enable a plurality of independent electrical communication channels to be formed between each said pin subassembly and each said plug subassembly.

19. The apparatus of claim 18, wherein the first annular interface element includes a beveled inner wall portion for supporting the electrically conductive coupling ring.

20. A method for forming a high density electrical interconnect apparatus for interfacing with remotely located electrical components, the method comprising:
- providing a housing having a plurality of recesses each having a predetermined configuration;
- supporting a substrate element within the housing;
- supporting a plurality of independent substrate interface connect subassemblies arranged in a planar grid on the substrate element;
- using a plurality of independent electrical interface connector subassemblies to form a plurality of independent electrical communication channels with the substrate interface connect subassemblies, wherein each said independent electrical interface connector subassembly is configured to include;
  - an over-molded substrate shaped generally in accordance with the predetermined configuration of the recesses of the housing, each one of the independent electrical interface connector subassemblies configured to be placed within an associated one of the recesses of the housing;
  - a separate cable assembly extending at least partially into the over- molded substrate; and
  - at least one of a plurality of independent pin subassemblies or a plurality of plug subassemblies electrically communicating with the cable assembly, and wherein the independent substrate interface connect subassemblies comprise the other one of the plurality of independent pin subassemblies or independent plug subassemblies, and where the independent plug subassemblies and the independent pin subassemblies connect to form the plurality of independent electrical communication channels.

21. The method of claim 20, further comprising using a second housing with an additional plurality of substrate interface connect subassemblies and an associated additional subplurality of interface connector subassemblies, the additional housing being the same in length and width as the housing and being positioned on the housing to form a multilayer, high density electrical interconnect apparatus.

22. A high density electrical interconnect apparatus for interfacing with remotely located electrical components, the apparatus comprising:
- a housing;
- a substrate element supported within the housing;
- a plurality of independent substrate interface connect subassemblies arranged in a planar grid on the substrate element; and
- plurality of independent electrical interface connector subassemblies, each said independent electrical interface connector subassembly including at least one of a plurality of independent pin subassemblies or a plurality of independent plug assemblies, and configured to be coupled to an associated subplurality of the substrate interface connect subassemblies, where the subplurality of the substrate interface connect subassemblies include the other one of the plurality of independent pin subassemblies or independent plug assemblies, to form a plurality of electrical communication channels with the remotely located electrical components;
- wherein the plug subassemblies are segmented in a plurality of separate groups, with each said separate group comprising a plurality of plugs arranged in a grid; and
- wherein each one of the independent electrical interface connector subassemblies includes a ribbon cable portion including a plurality of electrical conductors.

23. A high density electrical interconnect apparatus for interfacing with remotely located electrical components, the apparatus comprising:
- a housing;
- a substrate element supported within the housing;
- a plurality of independent substrate interface connect subassemblies arranged in a planar grid on the substrate element;
- plurality of independent electrical interface connector subassemblies, each said independent electrical interface connector subassembly including at least one of a plurality of independent pin subassemblies or a plurality of independent plug assemblies, and configured to be coupled to an associated subplurality of the substrate interface connect subassemblies, where the subplurality of the substrate interface connect subassemblies include the other one of the plurality of independent pin subassemblies or independent plug assemblies, to form a plurality of electrical communication channels with the remotely located electrical components; and
- wherein each one of the plurality of independent electrical interface connector subassemblies includes:

a plurality of electrical conductors;
an over-molded housing portion for at least one of supporting or at least partially housing the plurality of electrical conductors;
the over-molded housing portion further supporting each of at least one of the pin subassemblies or the plug subassemblies in a linear spaced apart arrangement; and
a ribbon cable portion for supporting a portion of the electrical conductors.

* * * * *